United States Patent

Bimczok et al.

[11] Patent Number: 5,961,999
[45] Date of Patent: Oct. 5, 1999

[54] METHOD OF SKIN CARE USING A SKIN CARE PREPARATION CONTAINING A BETAINE ESTER AND AN α-HYDROXY ACID

[75] Inventors: Rudolf Bimczok, Seeheim; Guenther Lang, Reinheim, both of Germany

[73] Assignee: Wella Aktiengesellschaft, Darmstadt, Germany

[21] Appl. No.: 09/123,264

[22] Filed: Jul. 28, 1998

Related U.S. Application Data

[63] Continuation-in-part of application No. 08/634,773, Apr. 19, 1996, abandoned.

[30] Foreign Application Priority Data

Jun. 8, 1995 [DE] Germany ............... 195 20 859

[51] Int. Cl.[6] .................................................. A61K 7/00
[52] U.S. Cl. .................. 424/401; 514/828; 514/844; 514/846; 514/847
[58] Field of Search .................. 424/401; 514/828, 514/844, 846, 847

[56] References Cited

U.S. PATENT DOCUMENTS

| 5,091,171 | 2/1992 | Yu et al. | 424/642 |
|---|---|---|---|
| 5,376,287 | 12/1994 | Borcher, Sr. et al. | 252/8.8 |
| 5,500,138 | 3/1996 | Bacon et al. | 252/8.8 |
| 5,545,350 | 8/1996 | Baker et al. | 510/517 |
| 5,574,179 | 11/1996 | Wahl et al. | 554/110 |

*Primary Examiner*—Jose' G. Dees
*Assistant Examiner*—Michael A. Williamson
*Attorney, Agent, or Firm*—Michael J. Striker

[57] ABSTRACT

The method of skin care includes applying a skin care preparation to the skin of an individual in an amount sufficient to moisturize the skin or to cause a reduction of skin wrinkling and a smoothing of the skin. The skin care preparation has a pH value of 1 to 7 and contains from 0.1 to 20 percent by weight of at least one betaine ester of formula (I)

$$R_1-O-CO-CH_2-N^+(CH_3)_3 A^- \qquad (I),$$

wherein $R_1$ is a branched or straight chain alkyl group having from 10 to 30 carbon atoms and A− is a cosmetically acceptable anion; and from 0.05 to 20 percent by weight of at least one α-hydroxy acid present as a free acid, or in a lactone form thereof, or as a skin-compatible salt thereof with an organic base or an inorganic alkali, and/or as stereoisomers thereof, as D, L, and/or DL form. The at least one α-hydroxy acid is selected from the group consisting of alkyl α-hydroxy acids, aralkyl α-hydroxy acids, aryl α-hydroxy acids, polyhydroxy α-hydroxy acids and polycarboxylic α-hydroxy acids represented by the following chemical structure:

$$Ra-\underset{\underset{OH}{|}}{\overset{\overset{Rb}{|}}{C}}-COOH$$

wherein Ra and Rb represent, independently of each other, H, F, Cl, Br, an aryl group, an aralkyl group made from an aryl group and an alkyl radical having 1 to 25 carbon atoms, a saturated or unsaturated, straight or branched chain alkyl group having 1 to 25 carbon atoms, a cyclic group having 5 or 6 members including carbon atoms, with the proviso that Ra and Rb are not the same, and the aryl, arylalkyl and alkyl groups may have at least one substituent selected from the group consisting of OH, CHO, COOH and alkoxy groups having from 1 to 9 carbon atoms.

9 Claims, No Drawings

METHOD OF SKIN CARE USING A SKIN CARE PREPARATION CONTAINING A BETAINE ESTER AND AN α-HYDROXY ACID

CROSS-REFERENCE

This is a continuation-in-part of U.S. patent application, Ser. No. 08/634,773, filed Apr. 19, 1996, now abandoned.

BACKGROUND OF THE INVENTION

The subject of the present invention is a new skin care composition and method of skin care using a preparation containing a betaine ester and an α-hydroxy acid for care of the skin.

The characteristics or properties of human skin are negatively influenced by many different types of factors. Thus it is put under stress by various environmental factors, such as dry atmospheric conditions and cold conditions, or by frequent contact with soap- or surfactant-containing cleaning agents. Cosmetic skin care compositions should preserve and regenerate the physiological balance of the skin surface, provide good conditions for continuous skin regeneration, simultaneously protect from outside influences and stabilize the skin. Skin care compositions, which are usually in the form of a skin cream or skin lotion, must have outstanding skin compatibility, allow easy distribution on the skin and must be rapidly absorbed without leaving behind a disturbing greasy appearance on the skin surface. The skin treated with the skin care composition should feel smooth and flexible after treatment.

Furthermore the skin care composition should produce a continuous action, since the active ingredients penetrate into the epidermis, cause a regeneration and moisturize the horny layer and thus lead to a smoothing of skin wrinkles.

Although a number of skin care composition based on different active ingredients are known up to now it has not been possible to provide a skin care composition which is completely satisfactory in regarding to all its properties—particularly its hydration effect on the horny layer, its wrinkle smoothing action, its skin compatiblity and its ability to provide a smooth and flexible skin feel.

SUMMARY OF THE INVENTION

It is an object of the invention to provide a new method of skin care based on a skin care preparation containing a betaine ester and an α-hydroxy acid that hydrates the skin, smooths wrinkles, produces a pleasant skin feel and has an outstanding skin compatibility.

According to the invention, the method includes applying a skin care preparation according to the invention to a region of the skin of an individual in an amount sufficient to moisturize the skin or to cause a reduction of skin wrinkling and a smoothing of the skin, wherein the skin care preparation according to the invention has a pH of 1 to 7 and contains from 0.1 to 20 percent by weight, preferably from 0.5 to 5 percent by weight, of at least one betaine ester of the formula (I):

$$R_1\text{—O—CO—CH}_2\text{—N}^+(CH_3)_3 A^- \qquad (I),$$

wherein $R_1$ is a branched or straight chain alkyl group having from 10 to 30 carbon atoms and $A^-$ is a cosmetically acceptable anion, i.e. skin-compatible, causing no skin irritation; and from 0.05 to 20 percent by weight, preferably 0.5 to 6 percent by weight, of at least one α-hydroxy acid present as a free acid or in a lactone form thereof, or as a skin-compatible salt thereof with an organic base or an inorganic alkali, and as stereoisomers thereof, as D, L, and/or DL form;

wherein the at least one α-hydroxy acid is selected from the group consisting of alkyl α-hydroxy acids, aralkyl α-hydroxy acids, aryl α-hydroxy acids, polyhydroxy α-hydroxy acids and polycarboxylic α-hydroxy acids represented by the following chemical structure:

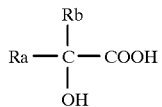

wherein Ra and Rb represent, independently of each other, H, F, Cl, Br, an aryl group, an aralkyl group made from an aryl group and an alkyl radical having 1 to 25 carbon atoms, a saturated or unsaturated, straight or branched chain alkyl group having 1 to 25 carbon atoms, a cyclic group having 5 or 6 members including carbon atoms, with the proviso that the Ra and Rb are not the same, and the aryl, arylalkyl and alkyl groups may have at least one substituent selected from the group consisting of OH, CHO, COOH and alkoxy groups having from 1 to 9 carbon atoms.

This method of providing skin care according to the invention satisfies the objects of the invention. Besides moisturizing the skin and smoothing skin wrinkles, the method of the invention produces a pleasant skin feel and the composition of the invention used in the method has outstanding skin compatibility. The good skin compatibility is especially surprising, since α-hydroxy acids can cause skin irritation based on their keratolytic action.

The preferred betaine esters of the formula (I) that are included in the skin care preparation used in the method of the invention are betaine octadecyl ester and betaine dodecyl ester.

The synthesis of the betaine esters of formula (I) is known and, for example, is described in published Japanese Patent Application 157 750 of 1983. The synthesis can occur by the direct esterification of fatty alcohols with betaine occurring as a by-product in sugar manufacture according to the following reaction mechanism:

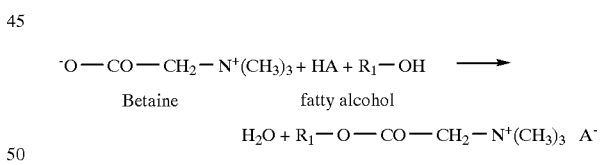

The betaine esters of the formula (I) are known from German Published Patent Application DE-OS 35 27 974 as components of acidic hair care compositions.

The betaine esters decompose into their constituents, fatty alcohol and betaine, in weakly acidic, neutral or alkaline pH ranges, while they are stable in the acidic pH range. The betaine esters of formula (I) produce a skin-smoothing action when used according to the method of the invention, while they are anti-irritating to the skin after hydrolytic cleavage to betaine and fatty alcohol.

The anion $A^-$ may be any cosmetically acceptable anion. The preferred $A^-$ are halogen anions, sulfate, methosulfate or phosphate, especially chloride or bromide.

The preparation used in the method according to the invention has very good skin compatiblity despite its content of (α-hydroxy acids, which especially can cause skin irritation with sensitive skin. The betaine esters of formula (I) are not only anti-irritating and anti-inflammatory but improve skin compatiblity of the α-hydroxy acids.

The skin care composition applied in the method according to the invention advantageously contains preferred α-hydroxy acids selected from the group consisting of citric acid, lactic acid, glycolic acid, malic acid, tartaric acid, salicylic acid, gluconic acid, glucuronic acid and saccharic acid. Citric acid and lactic acid are especially preferred.

In general, preferred embodiments of the skin care composition may contain at least one α-hydroxy acid is selected from the group consisting of 2-hydroxyethanoic acid, 2-hydroxypropanoic acid, 2-methyl-2-hydroxypropanoic acid, 2-phenyl-2-hydroxyethanoic acid, 2,2-diphenyl-2-hydroxyethanoic acid, 2-phenyl-2-methyl-2-hydroxyethanoic acid and 2-phenyl-3-hydroxypropanoic acid. Preferred alkyl α-hydroxy acids include 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodeconoic acid, 2-hydroxytetradecanoic acid, 2-hydroxyhexadeconic acid, 2-hydroxyoctadecanoic acid and 2-hydroxyeicosanoic acid. Preferred aralkyl α-hydroxy acids and aryl α-hydroxy acids comprise 2-phenyl-2-hydroxyethanoic acid, 2,2-diphenyl-2-hydroxyethanoic acid, 3-phenyl-2-hydroxypropanoic acid, 2-phenyl-2-methyl-2-hydroxyethanoic acid, 2-(4'-hydroxyphenyl)-2-hydroxyethanoic acid, 2-(4'-chlorophenyl)-2-hydroxyethanoic acid, 2-(3'-hydroxy-4'-methoxyphenyl)-2-hydroxyethanoic acid, 2-(4'-hydroxy-3'-methoxyphenyl)-2-hydroxyethnoic acid, 3-(2'-hydroxyphenyl)-2-hydroxypropanoic acid, 3-(4'-hydroxyphenyl)-2-hydroxypropanoic acid and 2-(3',4'-dihydroxyphenyl)-2-hydroxyethanoic acid. Preferred polyhydroxy α-hydroxy acids and polycarboxylic α-hydroxy acids include 2,3-dihydroxypropanoic acid; 2,3,4-trihydroxybutanoic acid; 2,3,4,5-tetrahydroxypentanoic acid; 2,3,4,5,6-pentahydroxyhexanoic acid; 2,3,4,5,6,7-hexahydroxyhepatnoic acid; 2-hydroxypropane-1,3-dioic acid; 2-hydoxybutane-1,4-dioic acid; 2,3-dihydroxybutane-1,4-dioic acid; 2-hydroxy-2-carboxypentane-1,5-dioic acid and 2,3,4,5-tetrahydroxyhexane-1,6-dioic acid.

The skin care preparation used in the method according to the invention may be present in the form of a solution, a suspension, a paste, a gel or an emulsion, however advantageously in the form of oil-in-water or water-in-oil emulsions, and may be packaged advantageously as facial water, skin cream, body lotion, facial packing or facial masking.

The skin care preparation used in the method according to the invention may contain at least one conventional cosmetic additive, especially a nonionic, cationic, amphoteric or zwitterionic surfactant, for example ethoxylated fatty alcohols with 12 to 18 carbon atoms, for example lauryl- cetyl- or stearyl alcohol ethoxylated with up to 40 mol ethylene oxide per mol, fatty alcohol, alkyl betaine, alkylaminobetaine, alkylsulfobetaine and fatty acid alkylamido betaine in amounts of 0.01 to 5.0 percent by weight; sequestering agents; emulsifiers; natural materials, such as Vitamins F and B6, D-panthenol; amino acids, such as betaine, cysteine, alanine, valine or tyrosine, or plant extracts, pigments, perfume oils in amounts of 0.5 to 5.0 percent by weight; turbidity inducing agents, such as ethylene glycol distearate in amounts of about 0.5 to 5.0 percent by weight; moisturizing agents, such as glycerol, polyols, hyaluronic acid and urea, in amounts of 0.05 to 20 percent by weight, advantageously 0.1 to 10 percent by weight; pearlescent agents, for example a mixture of fatty acid monoalkyolamide and ethylene glycol distearate, in amounts of about 1.0 to 10.0 percent by weight; thickeners, such as coconut fatty acid diethanolamide or hydroxyalkyl cellulose, in an amount of 0.1 to 1.0 percent by weight; buffer substances, such as sodium citrate or sodium phosphate, in amounts of 0.1 to 1.0 percent by weight; and dyes, such as fluorescein-sodium salt, Yellow ZN3 (C.I. 47 055), in an amount of 0.1 to 1.0 percent by weight; skin care additives, such as fatty acid esters, fatty alcohols and fatty acid glycerides; natural, modified natural or synthetic polymers, such as cationic, anionic or nonionic cellulose derivatives, chitosan, cationic chitin- or chitosan derivatives, care substances, such as lanolin derivatives and pantothenic acid, in amounts of 0.1 to 10 percent by weight; and light protecting agents, antioxidants; complex formers; cosmetic oils and waxes and preservatives, in so far as these additives appear to be useful and appropriate and are compatible with the ingredients of the preparation.

The pH-value of the skin care preparation used in the method according to the invention is preferably from 4 to 6 and may be adjusted with physiologically compatible organic or inorganic acids or bases, e.g. with benzoic acid, citric acid, formic acid or acetic acid, sorbic acid, sodium hydroxide, ammonia or monoethanolamine or triethanolamine, when it does not self-adjust because of the α-hydroxy acids contained in it. Acceptable salts of the α-hydroxy acids suitable for use in the preparation may be obtained by reacting the α-hydroxy acids with these same bases and acids.

The skin care preparation used in the method according to the invention may be water-free or contain up 99.5 % by weight water. Preferably the preparation used in the method according to the invention may contain from 50 to 80 percent by weight water.

The skin care preparation used in the method according to the invention may be sprayed by means of a propellant or with the aid of a mechanical spraying apparatus or foam producing apparatus or be delivered in a foam. The skin care preparation may also be applied in any of a variety of ways known to those skilled in the art.

If the skin care preparation used in the method according to the invention is applied by spraying with the help of a propellant, it preferably contains from 3 to 20 percent by weight of the propellant and is filled in a pressurized container. Lower alkanes, such a n-butane, i-butane and propane, or also their mixtures with dimethyl ether, and gaseous propellants under pressure, for example $N_2$, $N_2O$ and $CO_2$, and mixtures thereof.

Mechanical spraying apparatuses or foam producing apparatuses are those apparatuses which allow the spraying or foaming of a liquid without use of a propellant. A spray pump or an elastic container provided with a spray valve can be used as a suitable mechanical spraying apparatus, in which the skin care composition according to the invention is filled under pressure so that the elastic container stretches and is continuously delivered therefrom on contraction of the elastic container with the spray valve open.

The attachment described in European Patent Application EP-B 0 460 154 with the foam producing device can be used on an elastic container as a suitable mechanical foam producing apparatus.

The following examples illustrate the invention in detail.

EXAMPLES

Example 1
Skin Care Preparation

| | a) Oil Phase |
|---|---|
| 5.0 g | betaine octadecyl ester |
| 3.0 g | polyglyceryl-3-methylglucose distearate |
| 3.0 g | glyceryl stearate |
| 20.0 g | isopropyl stearate |
| 1.5 g | stearyl alcohol |
| 5.0 g | mineral oil |
| | b) Water Phase |
| 5.0 g | glycerol |
| 56.7 g | water |
| 0.3 g | perfume oil |
| 0.5 g | citric acid |
| 100.0 g | |

The skin care preparation according to example 1 is made by emulsifying the oil phase a) melted at about 75° C. and heated with stirring in the water phase b) comprising glycerol and water also at 75° C. Since the emulsion is cooled with uniform stirring at 45° C., the perfume oil c) is worked in. The pH-value is adjusted with citric acid to pH=4.

The skin care preparation according to example 1 is a soft cream, which, when applied to a predetermined area of the skin, is quickly absorbed in the skin, has outstanding skin compatibility and moistens the skin over a time period of several hours.

Example 2
Skin Cream in the form of an oil-in-Water Emulsion

| | a) Oil phase |
|---|---|
| 5.0 g | betaine octadecyl ester |
| 5.0 g | glyceryl stearate |
| 2.0 g | cetyl stearyl alcohol, ethoxylated with 12 Mol ethylene oxide |
| 4.0 g | cetyl stearyl alcohol, ethoxylated with 6 Mol ethylene oxide |
| 6.0 g | cetyl stearyl alcohol |
| 6.0 g | avocado oil |
| 4.0 g | mineral oil |
| 2.0 g | dimethyl polysiloxane |
| | b) Water phase |
| 4.0 g | glycerol |
| 3.0 g | glycolic acid |
| 2.0 g | salicylic acid |
| 1.0 g | citric acid |
| 1.0 g | betaine |
| 54.5 g | water |
| 0.5 g | perfume oil |
| 100.0 g | |

The oil phase a) is melted at 75° C. and is emulsified with stirring in the water phase b) heated at 55° C. After cooling at 45° C. the perfume oil is added and the emulsion is homogenized. The pH-value is adjusted with sodium hydroxide to 4.0.

The skin cream according to example 2 is a soft cream, which, when applied in a given amount to a predetermined area of the skin, is rapidly absorbed in the skin. It is characterized by an outstanding skin feel and compatibility. The cream causes a reduction of skin wrinkling after several treatments.

Example 3
Skin Cream in the form of an Water-in-oil Emulsion

| | a) Oil Phase |
|---|---|
| 4.00 g | polyglyceryl-2-sesquiisostearate |
| 4.00 g | hydrogenated castor oil, ethoxylated with 7 Mol ethylene oxide |
| 8.00 g | cetyl stearyl isononanoate |
| 8.00 g | squaline |
| 2.00 g | betaine octadecyl ester |
| 3.00 g | bees wax |
| 2.00 g | caranauba wax |
| | b) Water Phase |
| 61.00 g | water |
| 3.00 g | glycerol |
| 2.00 g | betaine dodecyl ester |
| 0.50 g | salicylic acid |
| 0.50 g | glycolic acid |
| 0.50 g | valine |
| 0.50 g | perfume oil |
| 1.00 g | tocopheryl acetate |
| 100.0 g | |

The oil phase a) is melted at 80° C. In a separate vessel the water phase b) is heated at 75° C. and added with stirring to the oil phase. After cooling at 50° C. the perfume oil and the tocopheryl acetate are worked in and the emulsion homogenized intensively.

The skin cream according to example 3 is a soft cream, which, when applied in a given amount to a predetermined area of the skin, is very easily distributed on the skin and produces a pleasant, smooth skin feel. Furthermore it has outstanding skin protective properties and outstanding skin compatibility.

Example 4
Oil-in-Water Body Lotion

| | a) Oil Phase |
|---|---|
| 10.0 g | cetyl stearyl octanoate |
| 3.0 g | sorbitan monostearate |
| 3.0 g | mixture of lauryl ester of sorbital and sorbitol anhydride ethoxylated with 20 Mol of ethylene oxide (CTFA-mark Polysorbate-20) |
| 2.0 g | dimethyl polysiloxane |
| 4.0 g | cetyl stearyl alcohol |
| 2.0 g | stearic acid |
| 0.8 g | betaine octadecyl ester |
| 0.1 g | para-hydroxybenzoic acid propyl ester |
| | b) Water Phase |
| 69.0 g | water |
| 0.2 g | betaine dodecyl ester |
| 5.0 g | glycerol |
| 0.2 g | salicylic acid |
| 0.3 g | citric acid |
| 0.1 g | allantoin |
| 0.3 g | perfume oil |
| 100.0 g | |

The oil phase a) is heated at 75° C. and is emulsified with stirring in the water phase b) heated at 70° C. After cooling at 45° C. the perfume oil is worked in and the emulsion homogenized. The body lotion so prepared is worked into the skin rapidly, causes a smooth pleasant skin feel and has an outstanding skin compatibility.

Example 5

Facial Tonic

| | |
|---|---|
| 2.00 g | betaine dodecyl ester |
| 1.00 g | citric acid |
| 4.00 g | urea |
| 2.00 g | salicylic acid |
| 2.00 g | lactic acid |
| 2.00 g | glycerol |
| 2.00 g | betaine |
| 0.10 g | hyaluronic acid |
| 69.9 g | water |
| 15.00 g | alcohol |
| 100.00 g | |

The composition according to example 5 has outstanding care and antiseptic properties and is suitable particularly for care of dirty and oily skin.

All percentages, unless otherwise indicated, are percentages by weight.

While the invention has been illustrated and described as embodied in a new method of skin care using a preparation containing a betaine ester and an α-hydroxy acid, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

We claim:

1. A method of skin care comprising applying a skin care preparation to a region of skin of an individual in an amount sufficient to moisturize said region of the skin or to cause a reduction of skin wrinkling and a smoothing of said region of the skin;

wherein the skin care preparation has a pH value of 1 to 7 and contains from 0.1 to 20 percent by weight of at least one betaine ester of formula (I)

$$R_1-O-CO-CH_2-N^+(CH_3)_3A^- \quad (I),$$

wherein $R_1$ is a branched or straight chain alkyl group having from 10 to 30 carbon atoms and $A-$ is a cosmetically acceptable anion;

from 0.05 to 20 percent by weight of at least one α-hydroxy acid present as a free acid or in a lactone form thereof, or as a skin-compatible salt thereof with an organic base or an inorganic alkali, and as stereoisomers as D and/or L, form;

wherein said at least one α-hydroxy acid is selected from the group consisting of alkyl α-hydroxy acids, aralkyl α-hydroxy acids, aryl α-hydroxy acids, polyhydroxy α-hydroxy acids and polycarboxylic α-hydroxy acids represented by the following chemical structure:

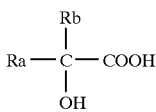

wherein Ra and Rb represent, independently of each other, H, F, Cl, Br, an aryl group, an aralkyl group made from an aryl group and an alkyl radical having 1 to 25 carbon atoms, a saturated or unsaturated, straight or branched chain alkyl group having 1 to 25 carbon atoms, a cyclic group having 5 or 6 members including carbon atoms, with the proviso that said Ra and Rb are not the same, and said aryl, arylalkyl and alkyl groups may have at least one substituent selected from the group consisting of OH, CHO, COOH and alkoxy groups having from 1 to 9 carbon atoms.

2. The method as defined in claim 1, wherein said at least one betaine ester is betaine octadecyl ester and/or betaine dodceyl ester.

3. The method as defined in claim 1, wherein said at least one α-hydroxy acid is selected from the group consisting of citric acid, lactic acid, glycolic acid, malic acid, tartaric acid, salicylic acid, gluconic acid, glucuronic acid and saccharic acid.

4. The method as defined in claim 1, wherein said at least one α-hydroxy acid is selected from the group consisting of 2-hydroxyethanoic acid, 2-hydroxypropanoic acid, 2-methyl 2-hydroxypropanoic acid, 2-phenyl-2-hydroxyethanoic acid, 2,2-diphenyl-2-hydroxyethanoic acid, 2-phenyl-2-methyl-2-hydroxyethanoic acid and 2-phenyl-3-hydroxypropanoic acid.

5. The method as defined in claim 1, wherein said alkyl α-hydroxy acids comprise 2-hydroxyethanoic acid, 2-hydroxypropanoic acid, 2-methyl-2-hydroxypropanoic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodeconoic acid, 2-hydroxytetradecanoic acid, 2-hydroxyhexadeconic acid, 2-hydroxyoctadecanoic acid and 2-hydroxyeicosanoic acid.

6. The method as defined in claim 1, wherein said aralkyl α-hydroxy acids and aryl α-hydroxy acids comprise 2-phenyl 2-hydroxyethanoic acid, 2,2-diphenyl-2-hydroxyethanoic acid, 3-phenyl-2-hydroxypropanoic acid, 2-phenyl-2-methyl-2-hydroxyethanoic acid, 2-(4'-hydroxyphenyl)-2-hydroxyethanoic acid, 2-(4'-chlorophenyl)-2-hydroxyethanoic acid, 2-(3'-hydroxy-4'-methoxyphenyl)-2-hydroxyethanoic acid, 2-(4'-hydroxy-3'-methoxyphenyl)-2-hydroxyethnoic acid, 3-(2'-hydroxyphenyl)-2-hydroxypropanoic acid, 3-(4'-hydroxyphenyl)-2-hydroxypropanoic acid and 2-(3',4'-dihydroxyphenyl)-2-hydroxyethanoic acid.

7. The method as defined in claim 1, wherein said polyhydroxy α-hydroxy acids and polycarboxylic α-hydroxy acids comprise 2,3-dihydroxypropanoic acid; 2,3,4-trihydroxybutanoic acid; 2,3,4,5-tetrahydroxypentanoic acid; 2,3,4,5,6-pentahydroxyhexanoic acid; 2,3,4,5,6,7-hexahydroxyhepatnoic acid; 2-hydroxypropane-1,3-dioic acid; 2-hydoxybutane-1,4-dioic acid; 2,3-dihydroxybutane-1,4-dioic acid; 2-hydroxy-2-carboxypentane-1,5-dioic acid and 2,3,4,5-tetrahydroxyhexane-1,6-dioic acid.

8. The method as defined in claim 1, wherein said skin care preparation contains from 0.5 to 5 percent by weight of said at least one betaine ester of the formula (I) and from 0.5 to 6 percent by weight of said at least one α-hydroxy acid.

9. The method as defined in claim 1, wherein said pH is from 4 to 6.

* * * * *